United States Patent [19]

Lemelson et al.

[11] Patent Number: 5,688,557
[45] Date of Patent: Nov. 18, 1997

[54] METHOD OF DEPOSITING SYNTHETIC DIAMOND COATINGS WITH INTERMEDIATES BONDING LAYERS

[76] Inventors: Jerome H. Lemelson, 868 Tyler Way, Incline Village, Nev. 89540; James G. Conley, 443 Jefferson Ave., Glencoe, Ill. 60022

[21] Appl. No.: 477,532

[22] Filed: Jun. 7, 1995

[51] Int. Cl.$^6$ .................................................... C23C 16/26
[52] U.S. Cl. ...................... 427/249; 427/577; 427/575; 427/419.7
[58] Field of Search ...................... 427/249, 577, 427/419.7, 575; 428/408; 423/446

[56] References Cited

U.S. PATENT DOCUMENTS

| | | |
|---|---|---|
| 2,411,867 | 12/1946 | Brenner . |
| 2,793,282 | 5/1957 | Steigerwald . |
| 2,861,166 | 11/1958 | Cargill, Jr. . |
| 2,947,610 | 8/1960 | Hall . |
| 2,968,723 | 1/1961 | Steigerwald . |
| 3,141,746 | 7/1964 | De Lai . |
| 3,207,582 | 9/1965 | Inoue . |
| 3,346,458 | 10/1967 | Schmidt . |
| 3,702,573 | 11/1972 | Nemeth . |
| 3,714,332 | 1/1973 | Rasquin et al. . |
| 3,913,280 | 10/1975 | Hall . |
| 3,916,506 | 11/1975 | Wolf . |
| 3,929,432 | 12/1975 | Caveney . |
| 3,959,557 | 5/1976 | Berry . |
| 4,054,426 | 10/1977 | White . |
| 4,084,942 | 4/1978 | Villalobos . |
| 4,385,880 | 5/1983 | Lemelson . |
| 4,394,400 | 7/1983 | Green et al. . |
| 4,434,188 | 2/1984 | Kamo et al. . |
| 4,490,229 | 12/1984 | Mirtich et al. . |
| 4,504,519 | 3/1985 | Zelez . |
| 4,554,208 | 11/1985 | MacIver et al. . |
| 4,594,294 | 6/1986 | Eichen et al. . |
| 4,621,031 | 11/1986 | Scruggs . |
| 4,663,183 | 5/1987 | Ovshinsky et al. . |
| 4,707,384 | 11/1987 | Schachner et al. . |
| 4,725,345 | 2/1988 | Sakamoto et al. . |
| 4,734,339 | 3/1988 | Schachner et al. . |
| 4,764,434 | 8/1988 | Aronsson et al. . |
| 4,776,862 | 10/1988 | Wiand . |
| 4,783,368 | 11/1988 | Yamamoto et al. . |
| 4,816,286 | 3/1989 | Hirose . |
| 4,832,993 | 5/1989 | Coulon . |
| 4,837,089 | 6/1989 | Araki et al. . |
| 4,849,199 | 7/1989 | Pinneo . |
| 4,859,493 | 8/1989 | Lemelson . |

(List continued on next page.)

FOREIGN PATENT DOCUMENTS

| | | |
|---|---|---|
| 57-106513 | 7/1982 | Japan . |
| 60-195094 | 10/1985 | Japan . |
| 61-106494 | 5/1986 | Japan . |
| 61-124573 | 6/1986 | Japan . |
| 62-72921 | 4/1987 | Japan . |
| 62-196371 | 8/1987 | Japan . |

OTHER PUBLICATIONS

Article: "Laser Method for Synthesis and Processing of Continuous Diamond Films on Nondiamond Substrates", Narayan et al., Apr. 19, 1991 (*Science*, vol. 252).

Article: "Growth mechanisms of diamond–like films formed by laser ablation of graphite," Bourdon et al., Aug. 20, 1990 (Publication)(*Applied Surface Science*).

Article: "The bonding of protective films of amorphic diamond to titanium", Collins et al., Dec. 16, 1991 (Publication), (*Journal of Applied Physics*, vol. 71, No. 7).

Article: "Low–Pressure, Metastable Growth of Diamond and 'Diamond–Like' Phases," John C. Angus & Cliff C. Hayman, Aug. 19, 1988, *Science*, p. 913.

*Mechanics of Materials*, Beer & Johnston, at pp. 316–317 (McGraw–Hill), 1981.

*Primary Examiner*—Roy V. King
*Attorney, Agent, or Firm*—Niro, Scavone, Haller & Niro

[57] ABSTRACT

A process is disclosed for making improved diamond coatings bonded to substrates by using intermediate bonding layers engineered to reduce the residual stress in the diamond coatings.

1 Claim, 9 Drawing Sheets

U.S. PATENT DOCUMENTS

| | | |
|---|---|---|
| 4,874,596 | 10/1989 | Lemelson . |
| 4,882,138 | 11/1989 | Pinnco . |
| 4,904,542 | 2/1990 | Mroczkowski . |
| 4,960,643 | 10/1990 | Lemelson . |
| 4,968,326 | 11/1990 | Wiand . |
| 4,974,498 | 12/1990 | Lemelson . |
| 5,021,628 | 6/1991 | Lemelson . |
| 5,040,501 | 8/1991 | Lemelson . |
| 5,067,826 | 11/1991 | Lemelson . |
| 5,096,352 | 3/1992 | Lemelson . |
| 5,114,745 | 5/1992 | Jones ................................ 427/113 |
| 5,124,179 | 6/1992 | Garg et al. . |
| 5,131,941 | 7/1992 | Lemelson . |
| 5,132,587 | 7/1992 | Lemelson . |
| 5,137,398 | 8/1992 | Omori et al. . |
| 5,161,728 | 11/1992 | Li . |
| 5,190,823 | 3/1993 | Anthony et al. . |
| 5,224,969 | 7/1993 | Chen et al. . |
| 5,239,746 | 8/1993 | Goldman . |
| 5,284,394 | 2/1994 | Lemelson . |
| 5,366,556 | 11/1994 | Prince et al. . |
| 5,370,195 | 12/1994 | Keshavan et al. . |
| 5,382,293 | 1/1995 | Kawarada et al. . |
| 5,391,407 | 2/1995 | Dearnaley . |
| 5,391,409 | 2/1995 | Shibata et al. . |
| 5,392,982 | 2/1995 | Li . |
| 5,401,543 | 3/1995 | O'Neill et al. . |
| 5,403,399 | 4/1995 | Kurihara et al. . |
| 5,415,704 | 5/1995 | Davidson . |

METHOD OF DEPOSITING SYNTHETIC DIAMOND COATINGS WITH INTERMEDIATES BONDING LAYERS

BACKGROUND OF THE INVENTION

Field of the Invention

This invention relates to methods of making new and improved diamond, "diamond-like carbon" (a-C) and "diamond-like hydrocarbon" (a-C:H) coatings bonded to substrates by using intermediate bonding layers engineered to reduce the residual stress in the diamond coatings, and to articles of manufacture made using such methods. The field of the invention also includes computer control systems for application of the diamond film via chemical vapor deposition or other techniques in such a way as to minimize the dynamic mismatch in strain during cooling of the coated product.

BACKGROUND OF THE INVENTION

Diamond, diamond-like carbon and diamond-like hydrocarbon coatings have been employed both to provide hard faces on engineered materials and as abrasive coatings on articles made from such materials. Typically such diamond films and/or particles are applied using some form of chemical vapor deposition (CVD) process. Such processes generally use thermal decomposition of a mixture of hydrogen and carbon compounds, preferably hydrocarbons, into diamond generating carbon atoms preferentially from the gas phase activated in such a way as to avoid substantially the deposition of graphitic carbon. The specific types of carbon compounds useful for CVD include C1—C4 saturated hydrocarbons such as methane, ethane, propane and butane; C1–C4 unsaturated hydrocarbons such as acetylene, ethylene, propylene and butylene; gases containing C and O such as carbon monoxide and carbon dioxide; aromatic compounds such as benzene, toluene, xylene, and the like; and organic compounds containing C, H, and at least one of oxygen and/or nitrogen such as methanol, ethanol, propanol, dimethyl ether, diethyl ether, methylamine, ethylamine, acetone, and similar materials (see U.S. Pat. No. 4,816,286). The molar concentration of carbon compounds in the hydrogen gas can vary from about 0.1% to about 5%, preferably from about 0.2% to 3%, and more preferably from about 0.5% to 2%. The resulting diamond film in such a deposition method is in the form of adherent individual crystallites or a layer-like agglomerates of crystallites substantially free from intercrystalline adhesion binder.

Such CVD processes are known to those skilled in the art, and ordinarily use some form of energy (for example, microwave radiation, as in U.S. Pat. No. 4,859,493 and in U.S. Pat. No. 4,434,188) to pyrolyze hydrocarbon gases such as methane at concentrations of about 1% to 2% in a low pressure (about 10 torr) hydrogen atmosphere, causing deposition of diamond or "diamond-like carbon" (a-C) or "diamond-like hydrocarbon" (a-C:H) particles or film on a nearby substrate. (Diamond and "diamond-like carbon" (a-C) coatings have an atomic hydrogen fraction of zero; for "diamond-like hydrocarbon" (a-C:H) coatings that fraction ranges from about 0.15 to about 0.6. Diamond coatings have atom number densities around 0.29 gram-atoms per cubic centimeter; "diamond-like carbon" (a-C) and "diamond-like hydrocarbon" (a-C:H) materials are characterized by atom number densities above 0.19 gram-atoms per cc.) It is also known to assist the CVD process using a variety of techniques including (1) pyrolysis by a hot tungsten filament intended to generate atomic hydrogen near the substrate (HFCVD); (2) supplying electrons by negatively biasing the filament as in electron-assisted chemical vapor deposition (EACVD); (3) creating a plasma using microwave energy or RF energy (PACVD; see U.S. Pat. Nos. 4,504,519 and 5,382,293); (4) using an argon ion beam to decompose the hydrocarbon feedstock, as in U.S. Pat. No. 4,490,229 and (5) using direct-current electrical discharge methods. See, generally, John C. Angus and Cliff C. Hayman, "Low-Pressure, Metastable Growth of Diamond and 'Diamond-like' Phases," *Science*, Aug. 19, 1988, at p. 913. The disclosures of the U.S. patent references cited above are incorporated by reference herein.

The ion beam deposition method typically involves producing carbon ions by heating a filament and accelerating carbon ions to selected energies for deposit on a substrate in a high vacuum environment ion beam systems use differential pumping and mass separation techniques to reduce the level of impurities in the carbon ion flow to the growing film.

The chemical vapor deposition and plasma enhanced chemical vapor deposition methods are similar in operation. Both methods use the dissociation of organic vapors (such as $CH_3OH$, $C_2H_2$, and $CH_3OHCH_3$) to produce both carbon ions and neutral atoms of carbon for deposit on a substrate. Plasma enhanced methods are described in U.S. Pat. No. 5,382,293 and No. 5,403,399.

Non-hydrogenated diamond-like carbon (a-C) films can be applied using a variety of techniques, which include magnetron sputtering, electron beam physical vapor deposition (EBPVD), laser photo-ablation, mass-filtered carbon ion beam deposition and cathodic arc plasma deposition, as described in U.S. Pat. No. 5,401,543 (incorporated by reference herein).

Sputtering deposition usually includes two ion sources, one for sputtering carbon from a graphite source onto a substrate, and another ion source for breaking the unwanted graphite bonds in the growing film. In the typical sputtering method, an argon ion sputtering gun sputters pure carbon atoms off of a graphite target within a vacuum chamber, and the carbon atoms are condensed onto a substrate. Simultaneously, another argon ion source bombards the substrate to enhance the breakdown of the graphite bonding in favor of a diamond-like $sp^3$ tetrahedral bond in the growing carbon film.

It is also known to apply polycrystalline diamond layers using sintering at simultaneous high pressures (50 kbar) and temperatures (1300° C.) to create conditions under which the diamond phase is thermodynamically stable, as in U.S. Pat. No. 5,370,195. And liquid-phase diffusion metallizing techniques also have been suggested for bonding diamond to certain types of substrates, as in U.S. Pat. No. 5,392,982.

Synthetic diamond-coated articles have found a wide variety of uses. U.S. Pat. No. 4,960,643, for example, discloses articles coated with synthetic diamond particles of controlled size, to which an overlying film, for example of chromium, has been applied to lubricate the diamond layer and to help resist scratching and wear. Other patents disclose various diamond-coated articles of manufacture, including bearings (U.S. Pat. No. 5,284,394); fasteners (U.S. Pat. No. 5,096,352); engine parts (U.S. Pat. Nos. 5,132,587 and 4,974,498) and the like.

The usefulness of diamond-coated engineered materials, and especially those made by CVD techniques, has been limited, however, by the large residual stress which remains in the finished composite products after coating is complete and the coated article has cooled. The stress arises from the very large differences in coefficients of thermal expansion (CTE) between the diamond coating (which have very low CTE's) and the substrates to which it is desired to bond it (often a metal having a much higher CTE). The substrate contracts during cooling more than the diamond film, leaving the diamond film in a permanent state of compressive stress which promotes spalling and cracking. The effect is aggravated by the high elastic modulus (low compressibility) of diamond compared to that of the substrate.

The rate of cooling of the substrate and the diamond film also affects the amount of stress, since diamond has a high thermal conductivity (promoting faster cooling) than metal substrates. Thus, the stress created during cooling may even exceed the static residual stress that remains when both the substrate and the film have reached the same final temperature.

Prior attempts to address the problem of fragility and crack propagation caused by residual stress have included providing soft, metallic braze layers, as in U.S. Pat. No. 4,968,326, sometimes molybdenum-based or carbide-based, as in U.S. Pat. No. 4,776,862. It has also been suggested to supply an intermediate braze layer in the form of multiple elements such as discs with dissimilar centers and edges between the metal and the diamond being bonded together. See U.S. Pat. No. 5,392,982. Such complex, multi-part intermediate layers are unsuited to situations in which uniform properties over a comparatively large coating area are desired and would also be difficult to adapt to CVD diamond film application techniques. Similarly, techniques that require drilling holes through the diamond layer to mechanically assist in bonding, as in U.S. Pat. No. 5,239,746, are excessively complex and costly for any high-volume applications. Additionally, the rough edges of such drill-through holes become crack initiation sites for spalling failures.

Others have suggested simultaneously co-depositing a silicon carbide onto a molybdenum substrate, along with the diamond. See U.S. Pat No. 5,190,823. Such a technique, however, requires weeks of deposition time and is impractical for commercial purposes. And, it fails to address the problem of ameliorating the differences in CTE between the diamond and the substrate: the SiC has a CTE much closer to that of diamond than to those of steel or aluminum alloys, as does $Si_3N_4$, which has also been suggested as a base for sinter coating. See U.S. Pat. No. 5,137,398. Mixing SiC or $Si_3N_4$ with diamond in a single, mixed coating does still leaves a likelihood of unacceptably high residual compressive stress. And, along with the low CTE, such materials lack the ductility and other desirable properties of metal substrates.

Still other investigators have suggested depositing multiple-layer polycrystalline diamond films by HFCVD, with cooling periods between layers of diamond film. See U.S. Pat. No. 5,124,179. This technique, however, also requires prolonged deposition times.

SUMMARY OF THE INVENTION

Figure 1:
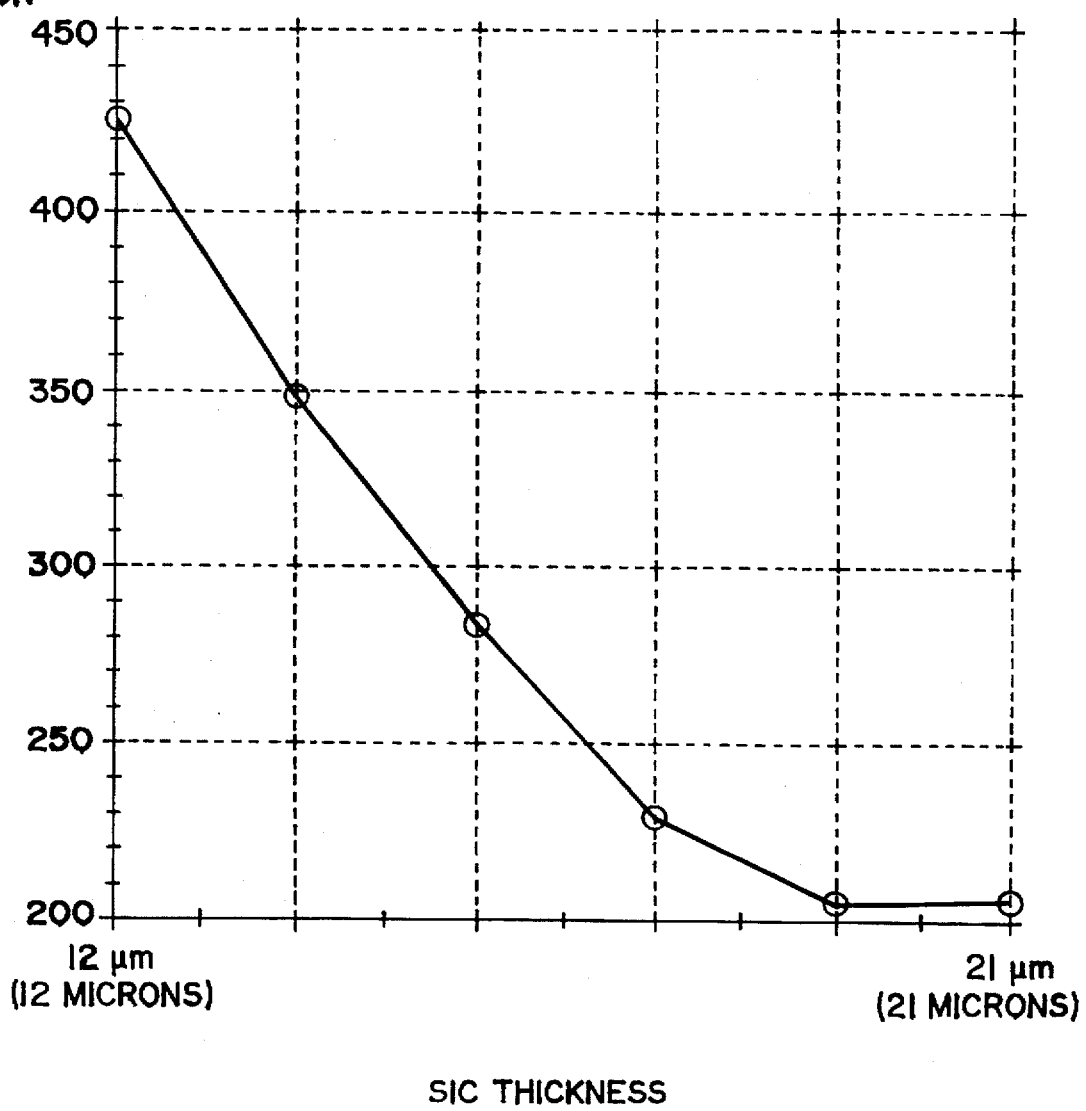
FIG. 1 shows the results of geometric element analysis of the stress derived from the Von Mises distortion energy criterion in a diamond coating applied to a semi-infinite flat plate of AlS380.0 having a varying thickness of SiC intermediate layer.

We find that the residual stress in diamond and diamond-like carbon thin film coatings applied to metal, cermet and ceramic substrates can be reduced to acceptably low levels by a combination of: (1) applying to the substrate an intermediate thin film coating of nitride or carbide of Al, Si, Ti, Ti-6Al-4V, Si-Al-V, Si-Al-O, W, B, Zr or Mo having certain specially predetermined properties based upon the particular substrate selected and (2) depositing a thin diamond, diamond-like carbon (a-C) or diamond-like hydrocarbon (a-C:H) film onto the intermediate layer by CVD while controlling the deposition rate, thickness, gas composition and temperature of the film and substrate to minimize dynamic imbalances between the transient strain on the substrate and the transient strain on the diamond coating (and, therefore, the transient stresses in the diamond coating).

Accordingly, it is an object of this invention to provide composite engineered materials having diamond or "diamond-like carbon" (a-C) or "diamond-like hydrocarbon" (a-C:H) coatings applied by CVD techniques but lacking most of the undesirable residual compressive stress induced by such techniques.

It is a further object of this invention to provide methods of creating such diamond-coated articles by computer control of CVD operating conditions.

It is still another object of this invention to provide articles having multi-layer coatings in which a metal, cermet or ceramic substrate has an overlying carbide- or nitride-forming layer to which a diamond film having reduced residual stress has been applied.

It is a further object of this invention to provide articles of manufacture having intermediate coatings and overlying diamond or diamond-like carbon coatings, such articles including without limitation PC boards; fasteners; bearings; cutting tools; valve seats; gears; blades; drill bits; dies; dental tools, medical prostheses or implants intended for long-term use inside the human body.

Further objects of this invention will be apparent to those skilled in the arts to which it pertains from the following detailed description.

DETAILED DESCRIPTION OF THE INVENTION

In its broadest embodiment, our invention comprises the provision of an intermediate thin layer of metal or ceramic having a specially predetermined range of three specific extensive properties (Poisson ratio, Young's modulus and coefficient of thermal expansion) between a substrate and an overlying layer of diamond, diamond-like carbon or diamond-like hydrocarbon. Substrates may be chosen from the group comprising metals, ceramics and cermets. Among metals for the substrate, we prefer to use aluminum castings in the 300 series (especially Al-8Si-3Cu); mild steel having 0.02% to 0.3% carbon, and more preferably 0.08% to 0.16% carbon; high carbon steel; Ti-Al-4V; or nickel-based superalloy. The aluminum alloy AlS380.0 (Al-8Si-3Cu) is most preferred. Suitable ceramics are high strength carbides, nitrides, silicides, oxides and borides of such metals, while appropriate cermets include metal matrix composites such as Al-SiC(p) with SiC contents ranging from 10% to 40%. Other suitable metal matrix composites including oxides such as $Al_2O_3$, nitrides such as $Si_3N_4$, and high melting temperature intermetallics such as NiAl, $Ni_3Al$, FeAl, $Fe_3Al$, and TiAl.

The intermediate layer may be comprised of elemental metals and/or carbides or nitrides of aluminum, silicon, titanium, tungsten, boron, molybdenum, zirconium or tantalum. Sialons (Si-Al-O-N ceramics, specifically $Si_3Al_3O_3N_5$) also may be used. So can commercially-available Ti-6Al-4V and Si-Al-V alloys. SiC is most preferred. Generally, the preferred thickness of the intermediate layer should be in the range of 10 to 50 micro-meters. The composition of the intermediate layer should be selected and certain properties predetermined in order to contract during cooling more slowly and to a lesser extent than the substrate, thereby decreasing the residual stress remaining in the diamond film when cooling is completed.

To manufacture diamond-coated articles using our invention, an article machined, cast or otherwise fabricated of the desired substrate is first coated with the selected intermediate layer. Such coating can be accomplished by a variety of techniques. One suitable method is metal vapor deposition (MVD), in which a layer of fine powdered intermediate metal (e.g. Ti) is applied to the surface of the substrate and then heated at pressures on the order of $10^{-6}$ torr to a temperature of 600° C. to 700° C. or higher (depending upon the vaporization temperature of the metal) for an hour or more, resulting in vaporization of the intermediate layer and condensation on the substrate. See, for example, U.S. Pat. No. 5,224,969, which describes an application of the technique. Alternately, electron beam physical vapor deposition (EBPVD) can be used. In that technique, the substrate article is placed in a high vacuum chamber in proximity to a sample of metal or ceramic desired to be used for the intermediate layer. The intermediate layer material is exposed to a focused electron beam which vaporizes it. The intermediate layer metal or ceramic material then condenses on the surface of the substrate. Other suitable techniques for applying the intermediate layer include sputtering, sintering of powder, electroplating, electroless deposition, diffusion coating and spray coating.

If an intermediate carbide or nitride layer is desired, such a layer may be formed by depositing a layer of the corresponding metal (for example, by MVD or EBPVD) and then carburizing or nitriding that layer by exposure to carbon or nitrogen at elevated temperatures.

Following application of the intermediate layer, a diamond, diamond-like carbon or diamond-like hydrocarbon coating is applied by CVD, laser ablation or other suitable technique. The total thickness of the diamond, diamond-like carbon or diamond-like hydrocarbon film is at least about 0.5 micro-meters, and preferably at least about 1 micro-meter. In more-sophisticated embodiments of our invention, described below, novel computer techniques are applied to control CVD operation so as to minimize residual compressive stress in the diamond coating. For purposes of this embodiment, however, it is assumed that ordinary CVD techniques are used.

Predetermination of Thickness For Specific Intermediate Layers

In any event, we find that predetermination and control of the thickness and thermophysical properties of the intermediate layer is very important to our invention. More specifically, the thickness of the intermediate layer should be chosen and controlled to reduce the stress derived from the Von Mises distortion energy criterion (see, for example, Beer & Johnston, *Mechanics of Materials* at pp. 316–17 (McGraw-Hill 1981)) to 500 MPa or less, and preferably to a level of about 250 MPa. What thickness is required to obtain that result depends primarily upon the CTE, Young's Modulus and Poisson ratio, as well as upon other properties of the substrate and the intermediate layer.

Figure 2:
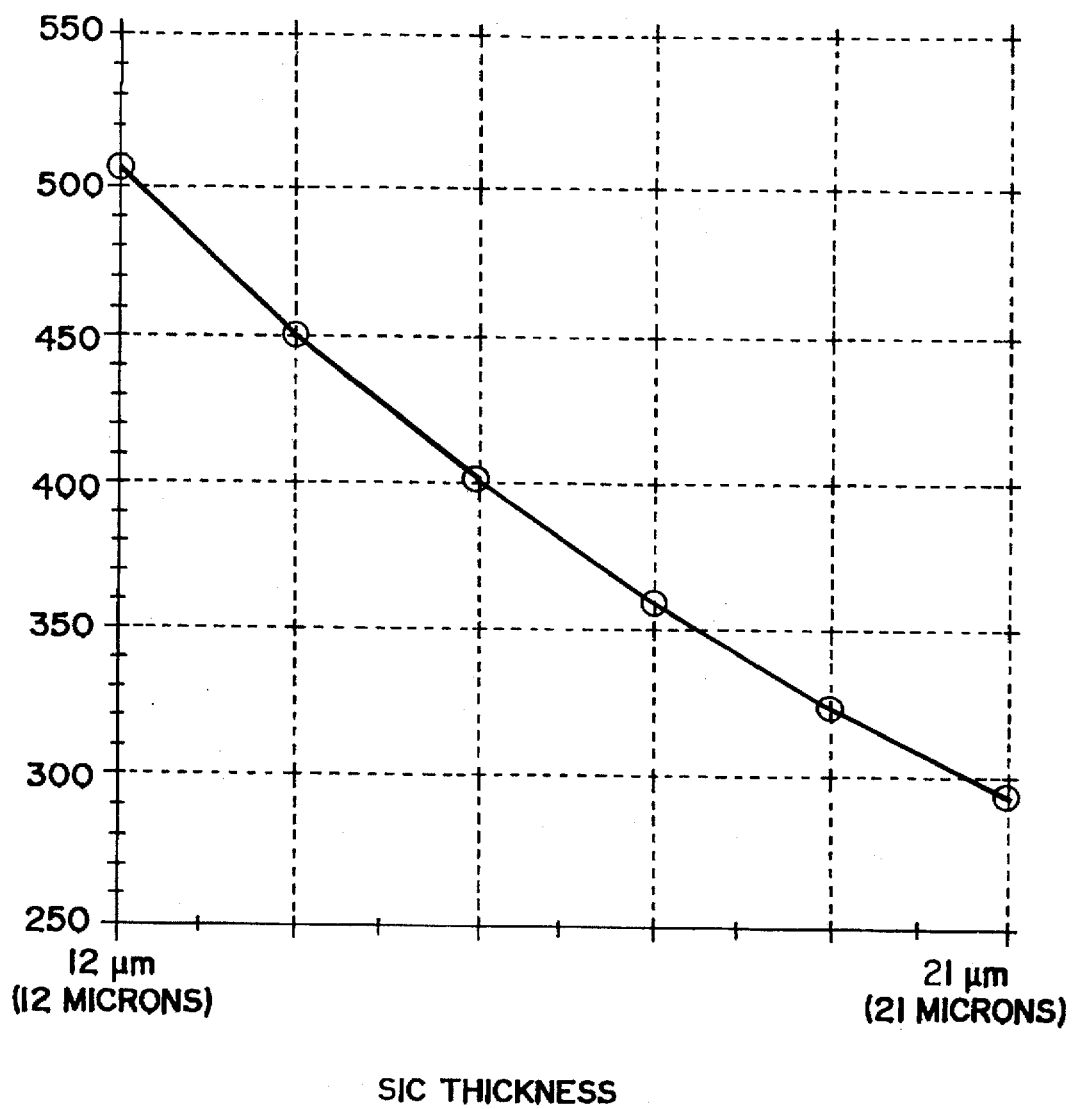
FIG. 2 shows the results of analysis of the stress derived from the Von Mises distortion energy criterion in a diamond coating applied to a semi-infinite flat plate of high-carbon steel having a varying thickness of SiC intermediate layer.

Turning to specific examples, FIG. 1 shows calculated results from a numerical model for very slow cooling of a semi-infinite flat AlS380.0 substrate to which a SiC intermediate layer has been applied, followed by a CVD layer of diamond having a thickness of about 1 to about 2 micro-meters. We find surprisingly that the stress derived from the Von Mises distortion energy criterion reaches a low level of slightly more than 200 MPa at a SiC thickness of about 19 micro-meters, whereupon further increase in the intermediate layer thickness yields little further reduction in stress in the diamond layer. We prefer, therefore, to use a minimum intermediate layer thickness corresponding to that point. The specific thickness, of course, depends upon the substrate/intermediate layer system chosen. For a high carbon steel substrate and a SiC intermediate layer, for instance, intermediate SiC layer thicknesses in excess of 21 micro-meters are needed to lower the stress given by the Von Mises distortion energy criterion much below 300 MPa. (FIG. 2).

Figure 3:
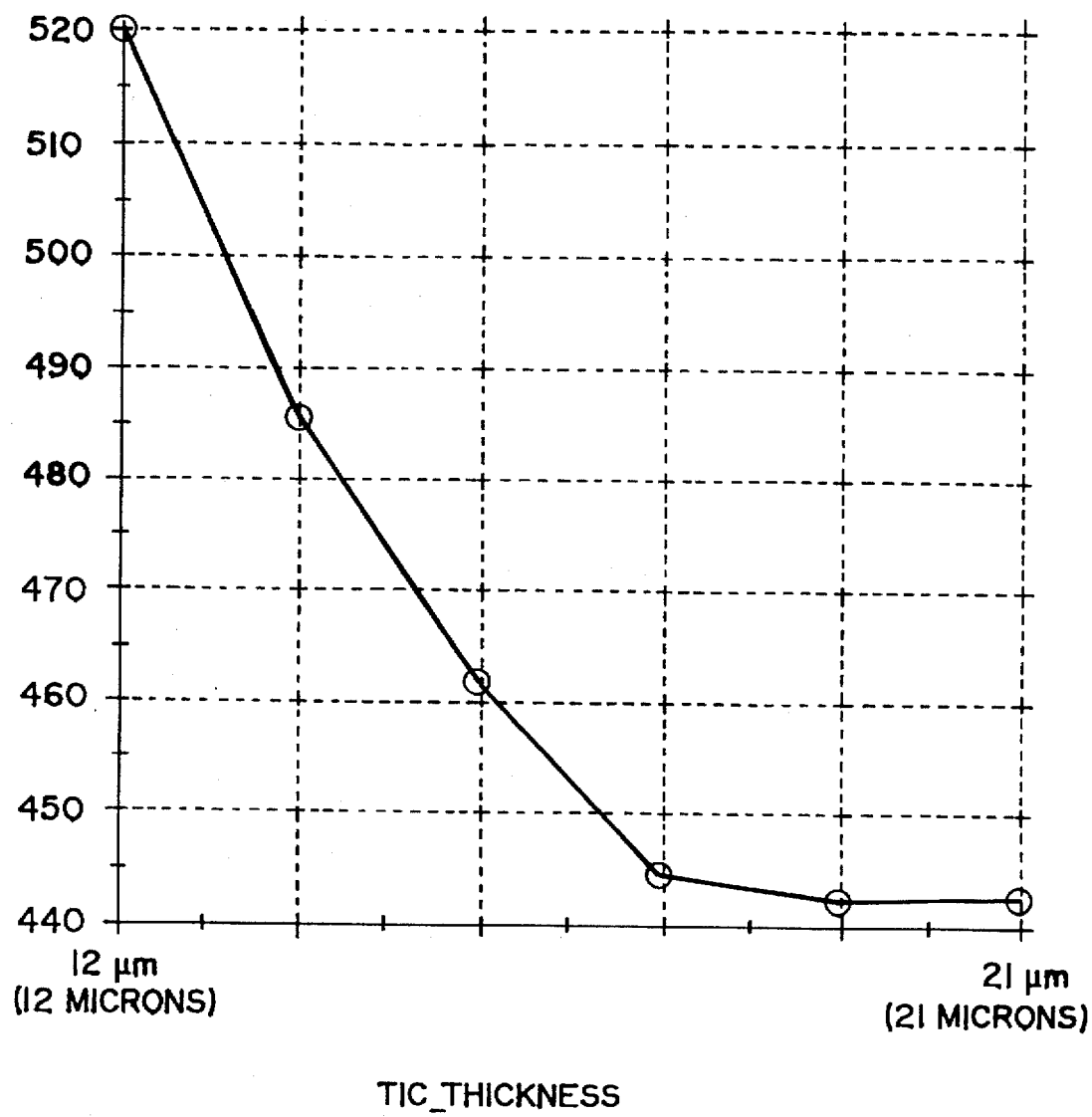
FIG. 3 shows the results of analysis of the stress derived from the Von Mises distortion energy criterion in a diamond coating applied to a semi-infinite flat plate of high-carbon steel having a varying thickness of TiC intermediate layer.
Figure 4:
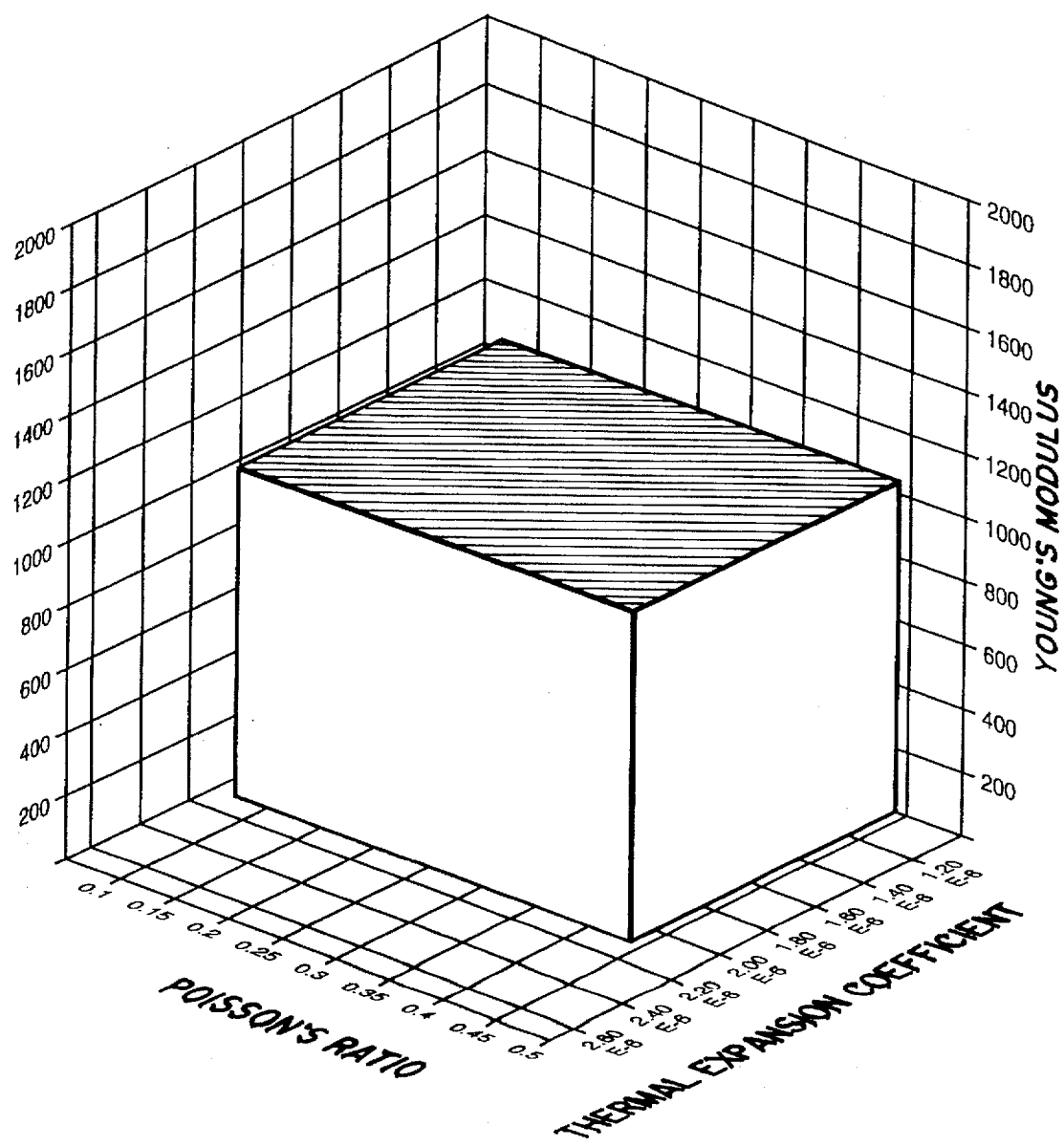
FIG. 4 shows the results of a more-general geometric element analysis of intermediate layer coatings ranging in thickness from 10 to 50 micro-meters applied to cast aluminum alloy substrates (specifically, Al-8Si-3Cu), illustrating the combined ranges of Young's modulus, Poisson ratio and thermal expansion coefficient in which the overlying diamond film will have a Von Mises stress below 250 MPa.
Figure 5:
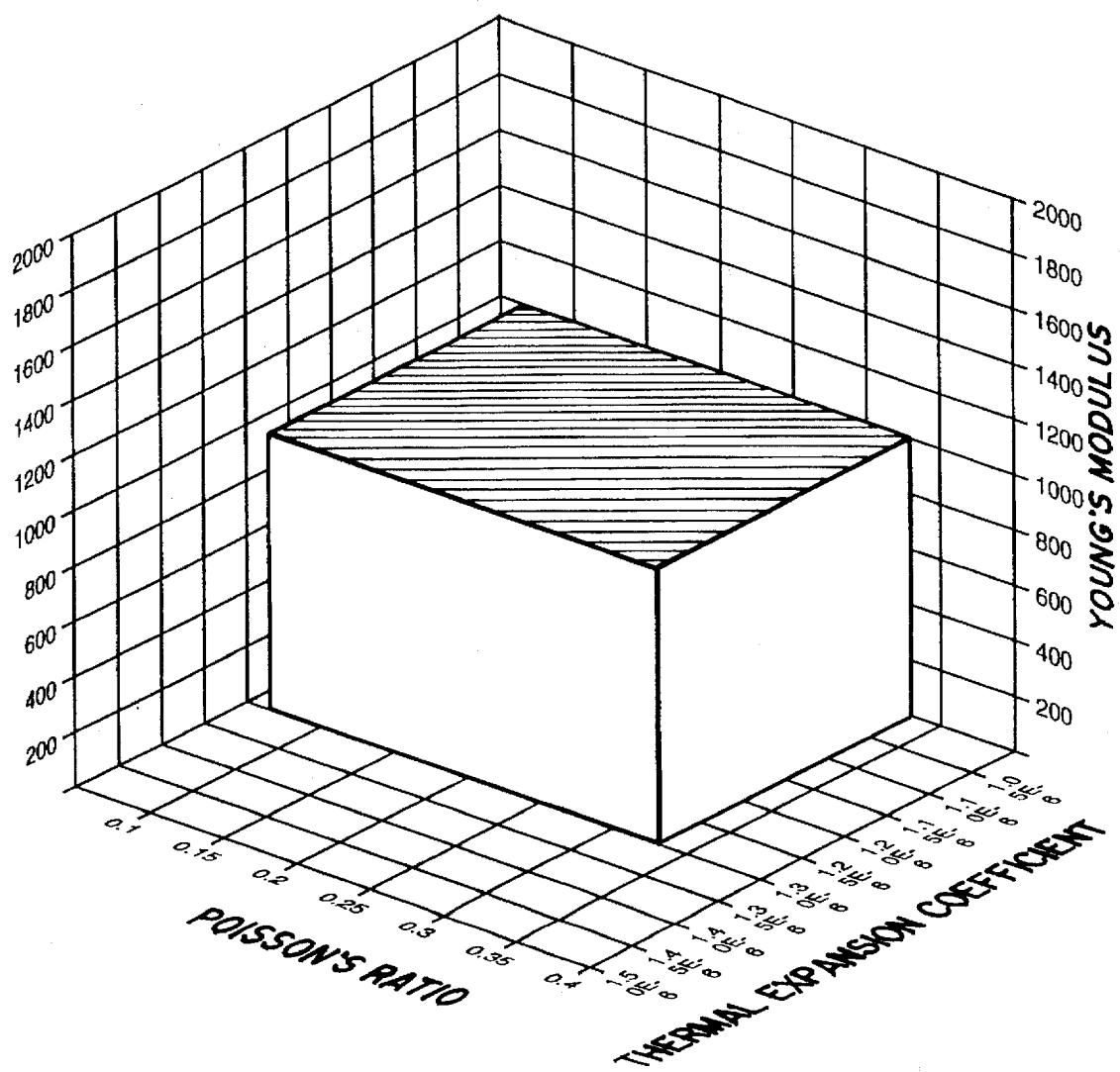
FIG. 5 shows the results of a more-general geometric element analysis of intermediate layer coatings ranging in thickness from 10 to 50 micro-meters applied to mild steel substrates (0.02% to 0.3% C), illustrating the combined ranges of Young's modulus, Poisson ratio and thermal expansion coefficient in which the overlying diamond film will have a Von Mises stress below 400 MPa.
Figure 6:
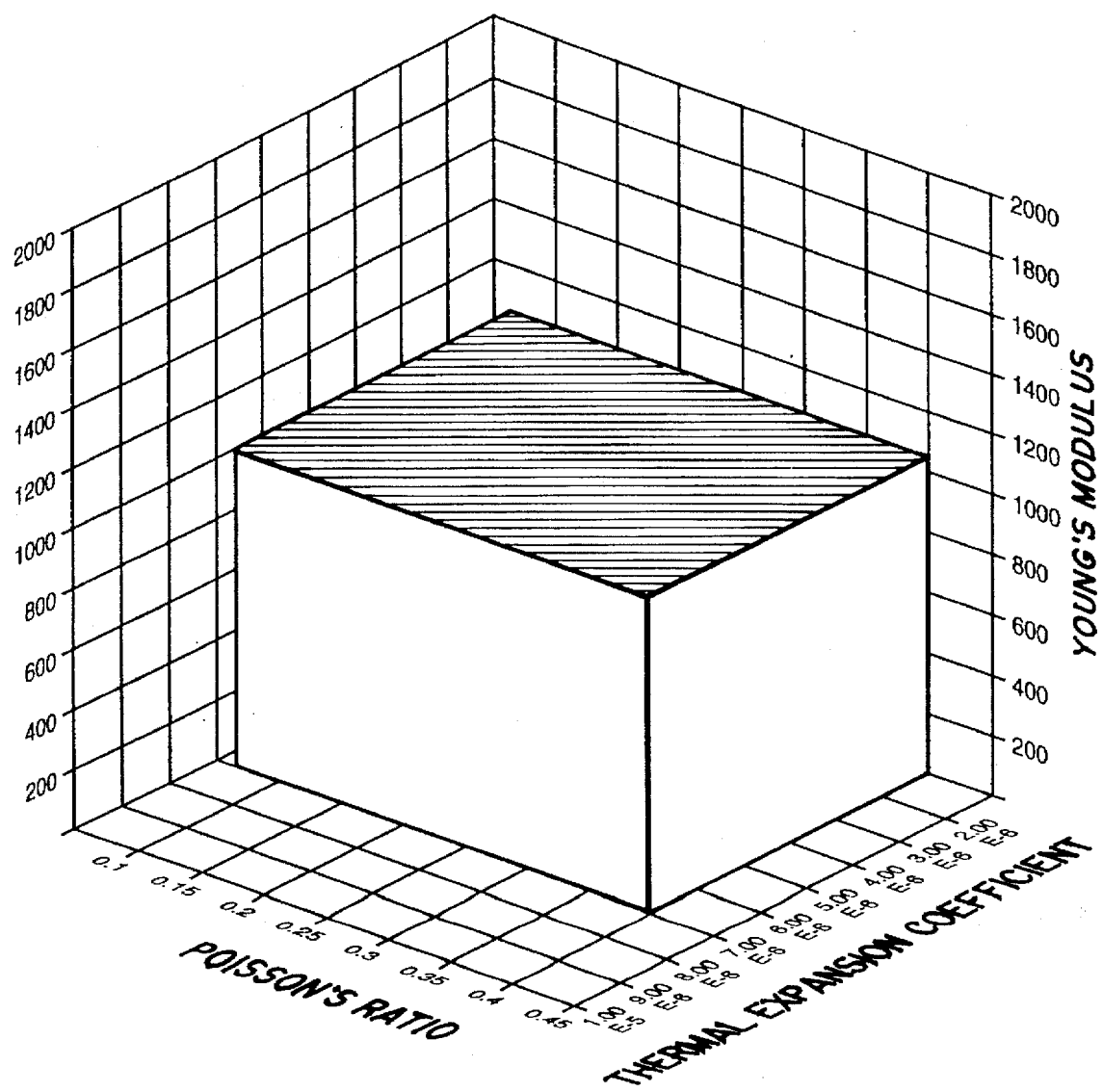
FIG. 6 shows the results of a more-general geometric element analysis of intermediate layer coatings ranging in thickness from 10 to 50 micro-meters applied to beta-titanium substrates (Ti-6Al-4V), illustrating the combined ranges of Young's modulus, Poisson ratio and thermal expansion coefficient in which the overlying diamond film will have a Von Mises stress below 500 MPa.
Figure 7:
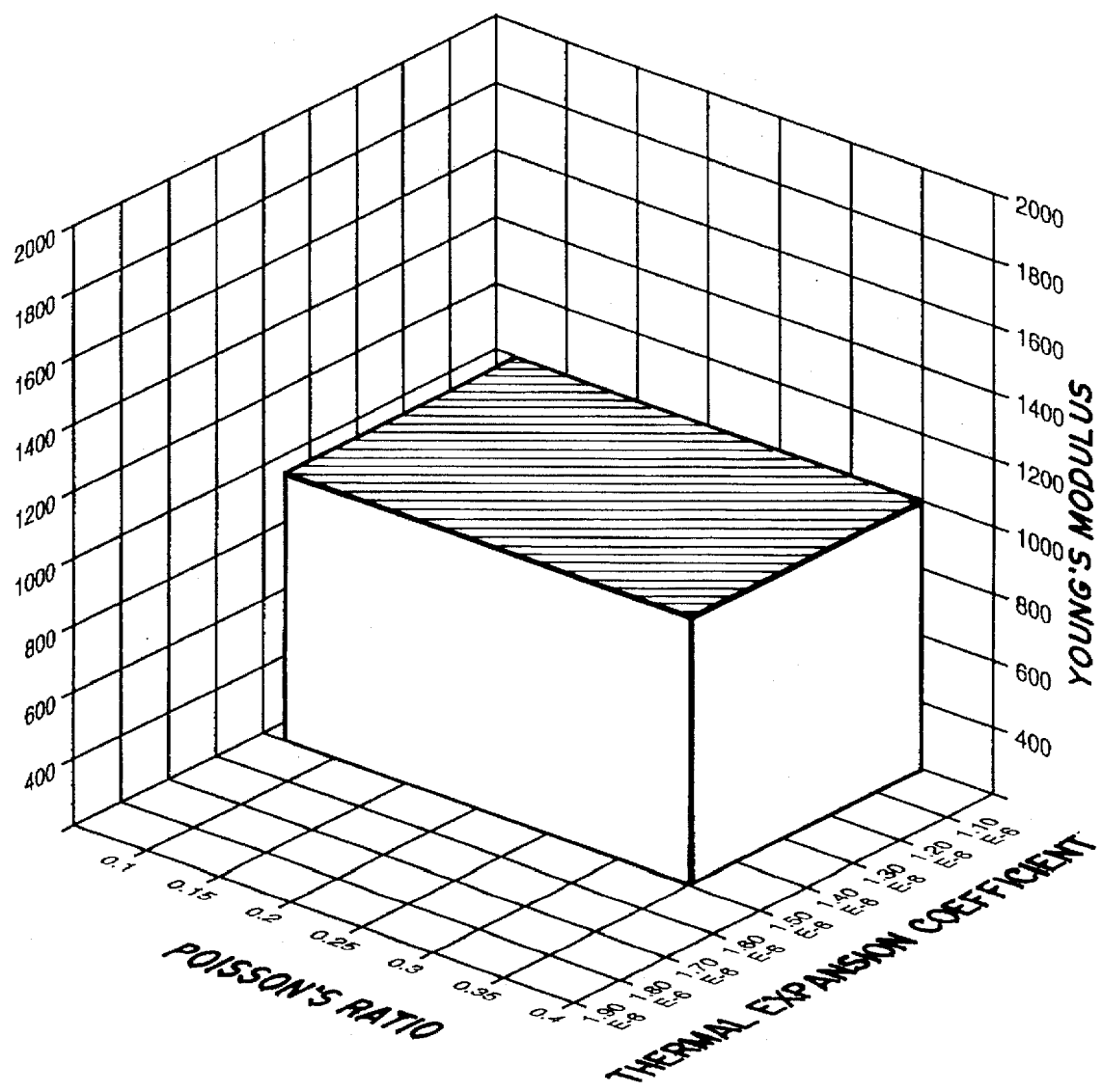
FIG. 7 shows the results of a more-general geometric element analysis of intermediate layer coatings ranging in thickness from 10 to 50 micro-meters applied to nickel-based superalloy substrate (Fe/20%–25% Ni-Al-Ti-Cr), illustrating the combined ranges of Young's modulus, Poisson ratio and thermal expansion coefficient in which the overlying diamond film will have a Von Mises stress below 400 MPa.
Figure 8:
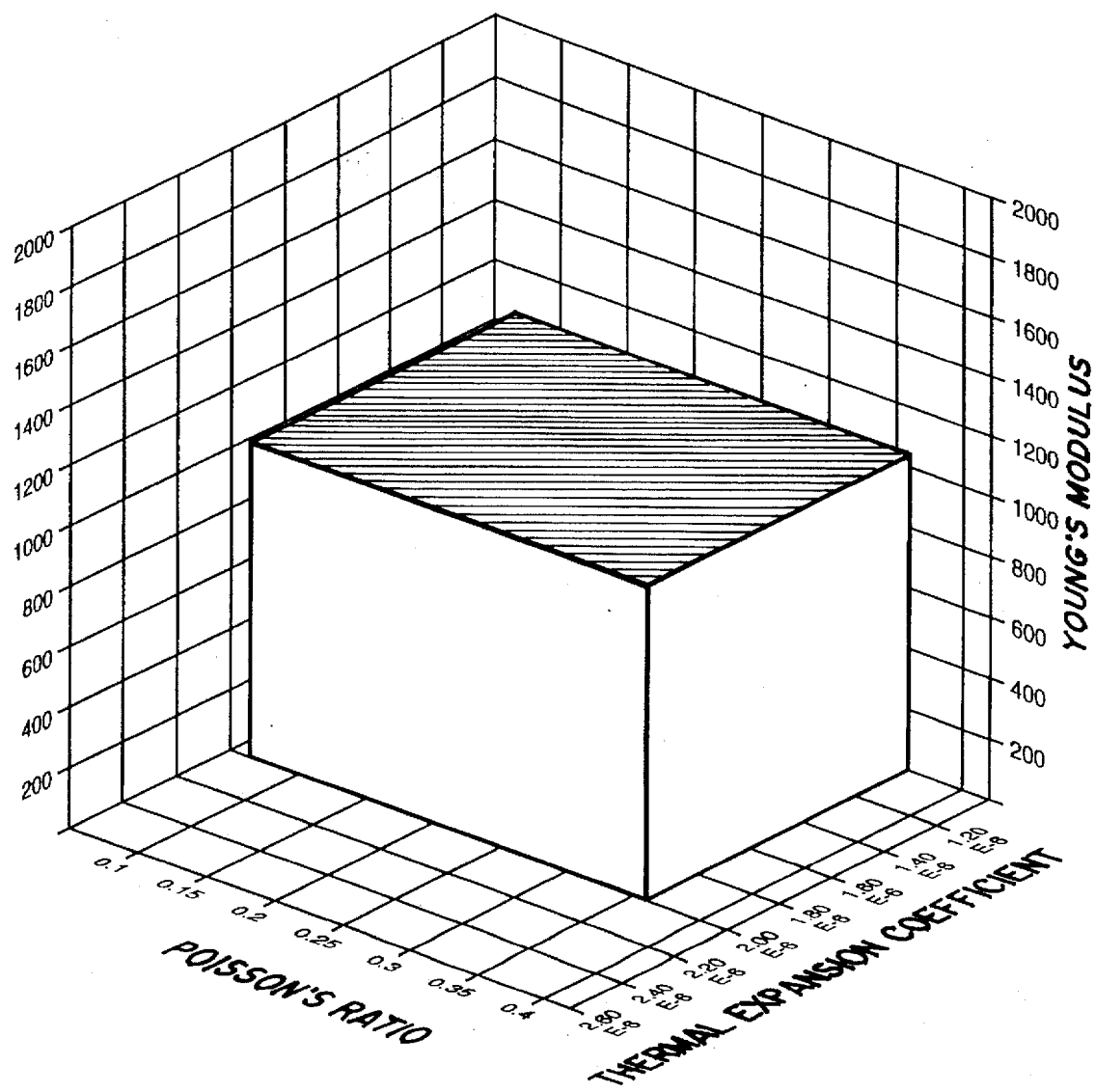
FIG. 8 shows the results of a more-general geometric element analysis of intermediate layer coatings ranging in thickness from 10 to 50 micro-meters applied to an Al-SiC (particulate) metal matrix composite substrate (Al/10%–40% SiC), illustrating the combined ranges of Young's modulus, Poisson ratio and thermal expansion coefficient in which the overlying diamond film will have a Von Mises stress below 250 MPa.

Using TiC instead of SiC with a high carbon steel (0.7%–1.7% C) substrate led to higher stresses than with a SiC intermediate layer on the same substrate. (Compare FIGS. 2 and 3). Titanium, however, is known to have advantages for fabricating abrasion-resistant and biocompatible implants for long-term use in the human body, as disclosed in U.S. Pat. No. 5,415,704. For such applications, the residual stress minimization techniques and structures of our invention may be particularly applicable with Ti intermediate layers. Our invention, however, is useful in fabricating biocompatible implants using any metal substrate. For example, the diamond coatings of our invention can help protect persons sensitive to nickel or chromium from adverse effects caused by the use of those metals in dental appliances (braces and the like). Moreover, because our diamond films provide efficient electrical insulation, the are also useful for minimizing the deleterious effects of galvanic action that results from interaction of body fluids with metal implants in the body.

For each substrate, predetermination of the substrate properties required to reach the "point of diminishing returns" as to the Von Mises stress level is an important aspect of our invention. Thickness alone can be predetermined as in the preceding examples, once an intermediate substrate composition has been selected, by using geometric element modeling techniques such as the Rasna MECHANICA geometric modeling computer program available from the RASNA Corporation of San Jose, Calif.; or by lab-scale tests to establish the minimum intermediate film thickness needed to reach the point where further stress reduction becomes de minimus.

All else being equal, intermediate layers made of materials with lower Young's moduli can be thinner (for equal stress reduction in the diamond layer) than those made with stiffer materials having higher Young's moduli. Similarly, an intermediate layer made of a material having a CTE closer to that of diamond can be thinner than one made of a material having a CTE further from that of diamond (presuming equal Young's moduli and Poisson's ratio).

Predetermination Of Required Properties For Any Intermediate Layer Composition

We find, surprisingly, that the interaction of three intermediate-layer parameters (Poisson ratio, Young's modulus and thermal expansion coefficient) is all that is required adequately to predetermine the net stress reduction effect with any given substrate material.

In the preferred embodiment of our invention, we use the RASNA Mechanica computer program (or other suitable numerical technique) to predetermine the range of intermediate layer physical properties necessary for residual Von Mises stress reduction for commercially-important substrate types and intermediate layer thicknesses by reference to just three easily-measured physical properties of the intermediate layer. Those general results appear in FIGS. 4 through 8. They reveal that each substrate exhibits a different range of those values of intermediate layer properties within which stress reduction in the diamond layer to the region of diminishing returns is achieved. At that level, for the particular substrate we say that the residual Von Mises stress has been minimized for practical purposes. Examples of the levels at which we say the residual Von Mises stress has been minimized appear in the following paragraph.

For the specific substrates modeled, the range of values within which our invention is most successful are as follows:

| Substrate Type | Intermediate Layer | | |
|---|---|---|---|
| | Young's Modulus GPa | Poisson Ratio | CTE $10^{-6}/°K$ |
| Cast Aluminum | 71–1000 | 0.07–0.44 | 1–21 |
| Mild Steel | 196–1000 | 0.065–0.33 | 1–13 |
| Ti-6Al-4V | 100–1000 | 0.065–0.40 | 1–7 |
| Ni Superalloy | 200–1000 | 0.065–0.35 | 1–15 |
| Al-SiC(p) | 85–1000 | 0.065–0.36 | 1–20 |

Similar analysis can be applied to other substrates, as well as to diamond-like carbon (a-C) or diamond-like hydrocarbon (a-C:H) overlying layers.

Thus, broadly stated, the preferred embodiment of our invention comprises selection of a substrate; application of geometric element analysis with reference to the CTE, Young's modulus and Poisson ratio of the intermediate layer to predetermine allowable ranges of those three properties; selection of an intermediate layer material whose properties lie within the predetermined allowable ranges, application of the intermediate layer (preferably in the 10 to 50 micrometer thickness range) followed by deposition of a diamond film over the intermediate layer using a suitable technique such as CVD.

Computer Control To Minimize Transient Stresses

The foregoing discussion relates to residual stress at room temperature equilibrium following CVD application of the diamond layer at approximately 800° C. That residual stress, however, may not be the maximum stress to which the diamond coating is subjected. The diamond coating in most applications tends to be much thinner than the substrate (as well as being exposed directly to the atmosphere, which the substrate may not be in the case, for example, of an object such as a ball bearing). In addition, the thermal conductivity of the diamond coating generally will be much higher than that of the substrate, whether the substrate is metal, cermet or ceramic. Thus, the thermal diffusivity of the diamond coating will be much greater than that of the substrate. As a result, after deposition the substrate temperature will tend to drop much more slowly than the temperature of the diamond layer if cooling is uncontrolled.

The temperature path followed by the intermediate layer cannot be generally predicted. It may tend to follow more closely either the substrate surface temperature or the diamond film/intermediate layer temperature, depending upon geometry and thermophysical properties of the substrate and intermediate layer. As a result, the maximum difference in strain between the diamond layer and the intermediate layer (as well as between the intermediate layer and the substrate) may not occur at room temperature. Thus, the diamond layer and/or the intermediate layer may generate maximum transient stresses at some intermediate point during cooldown rather than at the final equilibrium temperature. And in applications in which the finished product is exposed to elevated temperatures (internal combustion engine parts, for example), the problem may reverse itself during heatup in service, with highest stress at some intermediate temperature rather than at room temperature or at the final service temperature.

We find, therefore, that improved synthetic diamond and diamond-like carbon coatings can be prepared by microprocessor (computer) control of the CVD process used to apply the diamond film coating. The measured variables for such control include the substrate internal temperature profile and the surface temperature of the part being coated. (The latter temperature may be measured by non-contact techniques such as various types of pyrometry known to those skilled in the art.) Other measured variables may include the critical dimensions of the substrate and of the diamond coating itself (both thickness and, more importantly, length). Such dimensions may be measured by optical or direct contact techniques. Preferably, coating thickness is measured by X-ray diffraction. Still more preferably, X-ray techniques can be used to measure stress in the diamond layer directly.

The critical measured variables can be numerically combined to yield one or more objective functions representative of the transient stresses at any instant of time in the diamond film and/or the intermediate layer. Since it is desired generally to minimize such transient stresses, any of a number of optimization techniques (algorithms) can be numerically applied to the objective function, yielding a set of control points for process parameters that will minimize the transient and residual stress in both the diamond layer and the intermediate layer.

The CVD process parameters that will be controlled include substrate temperature; gas composition (e.g. methane concentration) and flowrate; microwave radiation frequency and intensity; pressure, coating thickness and substrate and coating cooling rates and thermal gradient through the intermediate coating and the diamond layer.

Where a multitude of small articles are being diamond coated (as in some of the embodiments disclosed in U.S. Pat. No. 4,859,493), both substrate and coating cooling rates are controlled primarily by varying fluidizing gas flowrates and temperatures. An auxiliary cooldown fluidized bed or series of beds at staged, intermediate temperatures and solids residence times also may be provided. In the case of CVD diamond films applied to larger substrates, substrate cooling rates may be moderated by auxiliary heaters or cooling devices, while the cooling rates of the coating may be controlled by varying radiation intensity and gas flowrates and temperatures. It may be desirable to utilize a glow discharge plasma method of applying the diamond or diamond-like carbon layer, since in such a process the substrate temperature and conditions can be controlled independently of the plasma temperature, as described in U.S. Pat. No. 4,394,400.

Figure 9:
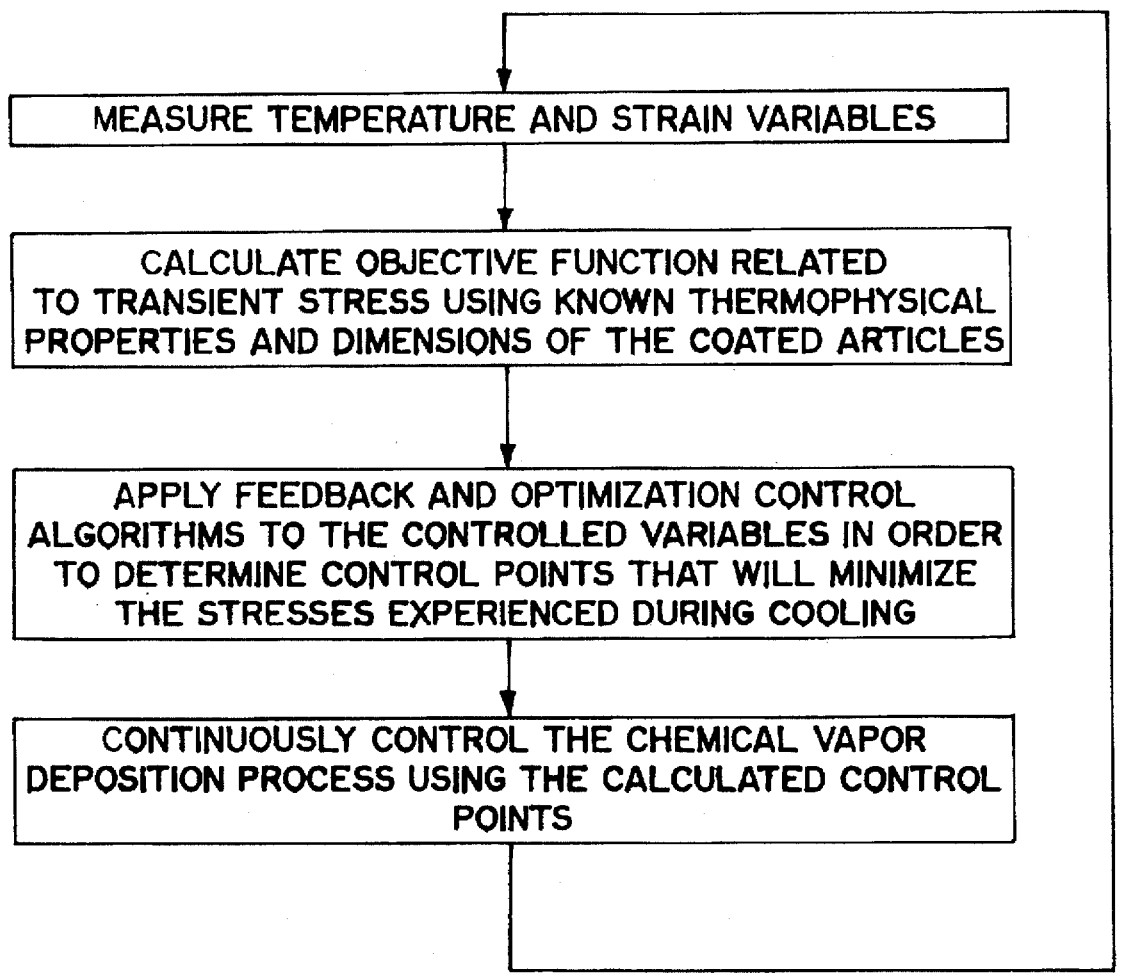
FIG. 9 shows a control scheme for minimizing the stress in the diamond layer by optimization of an objective function related to that stress.

In either event, the general control strategy (illustrated in FIG. 9) is as follows: (1) measure temperature and strain variables; (2) use known thermophysical properties and dimensions of the coated articles to calculate objective functions related to stresses in the coating; (3) apply feedback and optimization control algorithms to the controlled variables in order to minimize the stresses experienced in the substrate, the intermediate layer and the diamond thin film during cooling of the articles. In this fashion superior coatings can be obtained, since the maximum transient stress to which the coating has been subjected during manufacture will have been minimized.

It will be apparent to those of ordinary skill in the art that many changes and modifications could be made while remaining within the scope of our invention. For example, the dynamic stress minimization method disclosed above could be applied to diamond and diamond-like carbon and diamond-like hydrocarbon film deposition techniques other than CVD, such as laser ablation. We intend to cover all such equivalent articles of manufacture and processing methods, and to limit our invention only as specifically delineated in the following claims.

We claim:

1. A process for applying a diamond coating to a substrate comprising:
   a. coating said substrate with an intermediate coating selected from the group consisting of carbides and nitrides,
   b. applying said diamond coating by chemical vapor deposition (CVD) while continuously measuring at least one of the substrate internal temperature, the surface temperature of the substrate and the critical dimensions of the substrate and diamond coating;
   c. continuously calculating from said measurements by means of a computer an objective function related to the transient stress in said diamond coating;
   d. numerically applying to said objective function on a continuous basis a feedback optimization algorithm to yield control points for at least one of the substrate temperature, CVD gas composition, CVD gas flowrate, microwave radiation intensity, CVD operating pressure, substrate cooling rate and coating cooling rate, said optimization algorithm being designed to minimize the transient stress in said diamond coating; and
   e. continuously controlling at least one of said control points based on the results obtained from said optimization algorithm to minimize the transient stress in said diamond coating.

* * * * *